US006531298B2

(12) United States Patent
Stafford et al.

(10) Patent No.: US 6,531,298 B2
(45) Date of Patent: *Mar. 11, 2003

(54) FACTOR IX ANTIHEMOPHILIC FACTOR WITH INCREASED CLOTTING ACTIVITY

(75) Inventors: Darrel W. Stafford, Carrboro, NC (US); Jin Li Chang, Chapel Hill, NC (US)

(73) Assignee: The University of North Carolina at Chapel Hill, Chapel Hill, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 133 days.

(21) Appl. No.: 09/118,748

(22) Filed: Jul. 17, 1998

(65) Prior Publication Data

US 2002/0031799 A1 Mar. 14, 2002

Related U.S. Application Data

(60) Provisional application No. 60/053,571, filed on Jul. 21, 1997.

(51) Int. Cl.[7] .......................... C12P 21/02; C12N 15/12; C12N 1/00; C12N 5/00; C12N 15/63

(52) U.S. Cl. .................. 435/69.6; 435/69.1; 435/252.3; 435/254.11; 435/325; 435/410; 435/226; 536/23.2; 530/381

(58) Field of Search ........................... 435/320.1, 252.3, 435/325, 410, 254.11, 69.1, 69.6, 226; 536/23.2; 530/381

(56) References Cited

U.S. PATENT DOCUMENTS

| | | | |
|---|---|---|---|
| 4,994,371 A | 2/1991 | Davie et al. | 435/6 |
| 5,521,070 A | 5/1996 | Meulien | 435/69.1 |

FOREIGN PATENT DOCUMENTS

| | | |
|---|---|---|
| EP | 0 107 278 B1 | 11/1989 |
| EP | 0 373 012 B1 | 2/1995 |

OTHER PUBLICATIONS

Bajaj et al.; Experimental and Theoretical Evidence Supporting the Role of Gly[363] in Blood Coagulation Factor Ixa (Gly[193] in Chymotrypsin) for Proper Activation of the Proenzyme; *Journal of Biological Chemistry*; 265:2956–2961 (1990).

Banner et al.; The crystal structure of the complex of blood coagulation factor VIIa with soluble tissue factor; *Nature* 380:41–46 (1996).

Bottema et al.; Missense Mutations and Evolutionary Conservation of Amino Acids: Evidence That Many of the Amino Acids in Factor IX Function as "Spacer" Elements; *Am J. Hum. Genet.* 49:820–838 (1991).

Chang et al.; Abstract Replacing the First Epidermal Growth Factor Like Domain of Factor IX With That of Factor VII Enhances Clotting Activity, *Thrombosis and Haemostasis Abstracts*; 73:p 1202 (Jun. 1995).

Evans et al.; Canine hemophilia B resulting from a point mutation with unusual consequences; *Proc. Natl. Acad. Sci. USA* 86:10095–10099 (Dec. 1989).

Geddes et al.; A Moderate Form of Hemophilia B is Caused by a Novel Mutation in the Protease Domain of Factor IX; *The Journal of Biological Chemistry* 264 4689–4697 (1989).

Giannelli et al.; Haemophilia B: database of point mutations and short additions and deletions; *Nucleic Acids Research* 18:4053–4059 (1990).

Ketterling et al.; The Rates of G:C→T:A and G:C→C:G Transversion at CpG Dinucleotides in the Human Factor IX Gene American J Human Genetics 54:831–835 (1994).

Kisiel et al.; Proteolytic Inactivation of Blood Coagulation Factor IX by Thrombin; *Blood* 66:1302–1308 (1985).

Koeberl et al.; Functionally Important Regions of the Factor IX Gene Have a Low Rate of Polymorphism and a High Rate of Mutation in the Dinucleotide CpG; *Am. J. Hum. Genet.* 45:448–457 (1989).

Miyata et al.; Factor IX Amagasaki: A New Mutation in the Catlytic Domain Resulting in the Loss of Both Coagulant and Esterase Activities; *Biochemistry* 30:11286–11291 (1991).

*Primary Examiner*—Gabrielle Bugaisky
(74) *Attorney, Agent, or Firm*—Myers Bigel Sibley & Sajovec

(57) ABSTRACT

A non-naturally occuring Factor IX protein having an amino acid substitution at amino acid position 338 is provided. Preferred substitutions include the substitution of analanine, leucine, or valine for the arginine at amino acid position 338. Factor IX of the present invention is non-naturally occuring (e.g., does not contain only an arginine to proline substitution at amino acid position 338). Factor IX proteins of the invention are useful for facilitating blood clotting in subjects in need thereof, such as subjects afflicted with hemophilia B. Pharmaceutical formulations comprising Factor IX of the invention are provided, along with nucleic acids encoding the factor and vectors containing such nucleic acids.

12 Claims, 5 Drawing Sheets

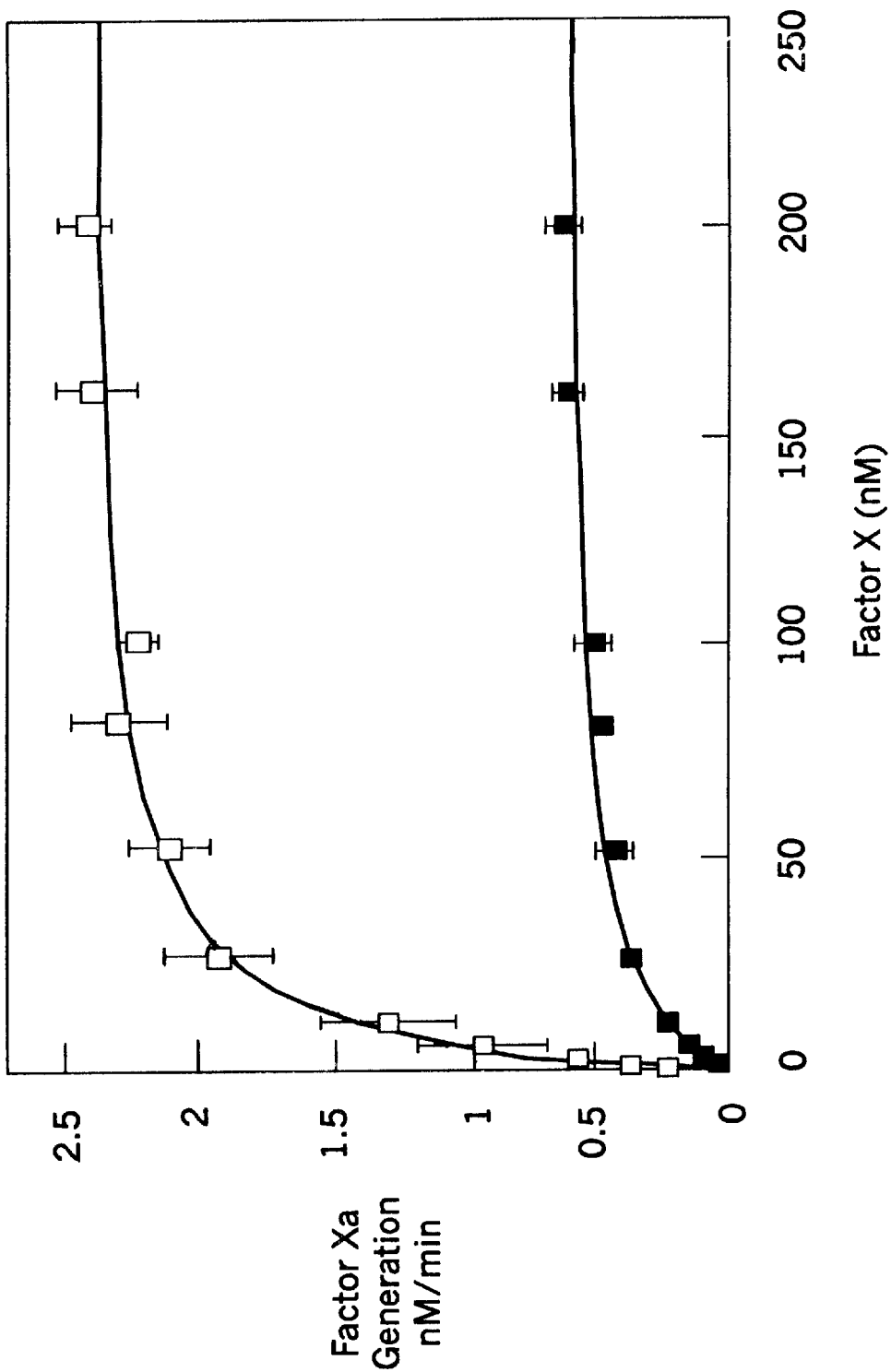

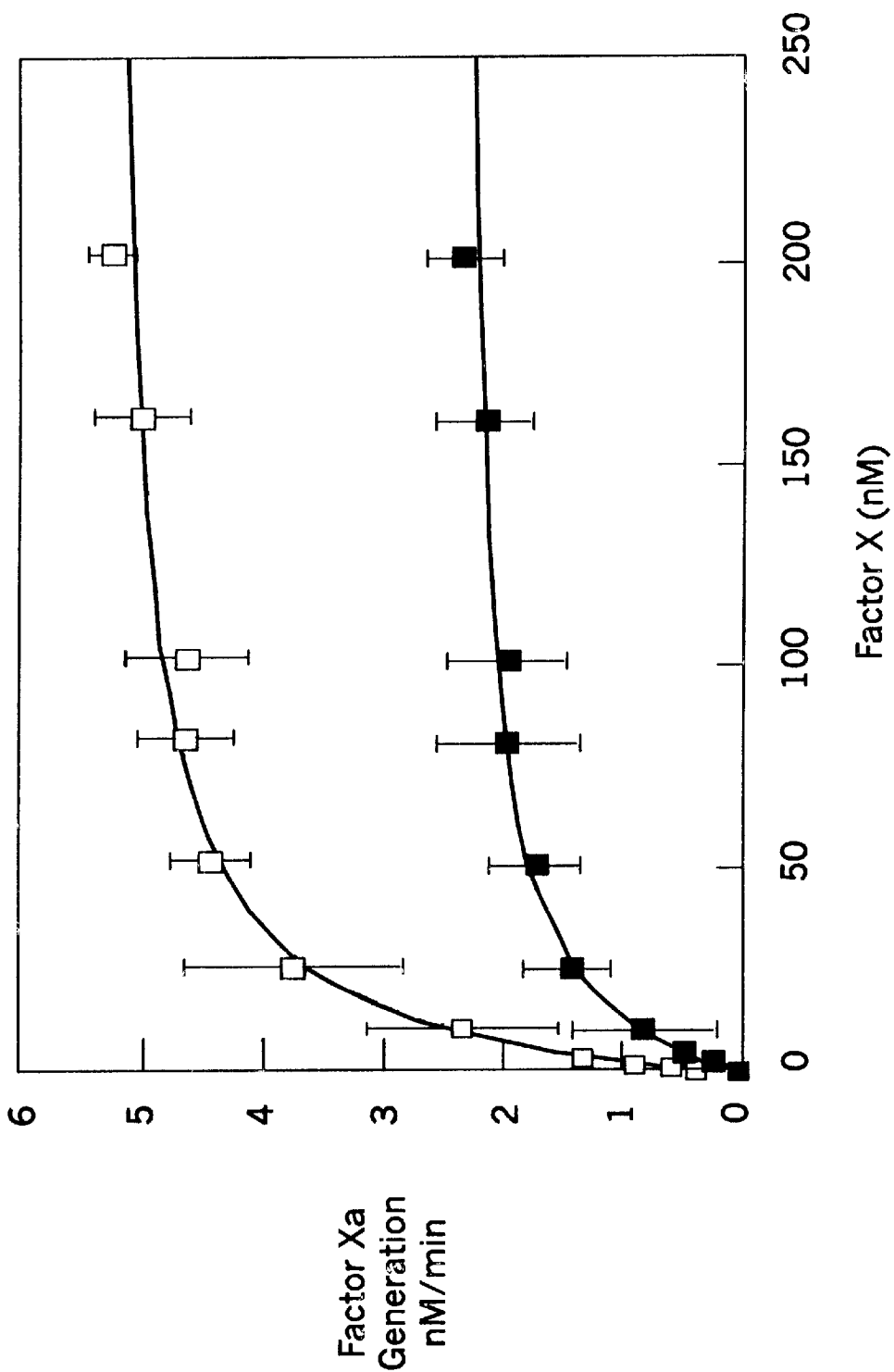

SEQUENCE LISTING

<160> NUMBER OF SEQ ID NOS: 2

<210> SEQ ID NO 1
<211> LENGTH: 2792
<212> TYPE: DNA
<213> ORGANISM: Homo sapiens
<220> FEATURE:
<223> OTHER INFORMATION: Description of Artificial Sequence:  sequence
      of human factor IX-R338A
<220> FEATURE:
<221> NAME/KEY: CDS
<222> LOCATION: (156)..(1400)

<400> SEQUENCE: 1

```
ggatccagat ctccaccatg cagcgcgtga acatgatcat ggcagaatca ccaggcctca      60
tcaccatctg cctttttagga tatctactca gtgctgaatg tacagttttt cttgatcatg     120
aaaacgccaa caaaattctg aatcggccaa agagg tat aat tca ggt aaa ttg         173
                                      Tyr Asn Ser Gly Lys Leu
                                        1               5 gaa gag ttt gtt caa ggg aac ctt gag aga gaa tgt atg gaa gaa aag        221
Glu Glu Phe Val Gln Gly Asn Leu Glu Arg Glu Cys Met Glu Glu Lys
                10                  15                  20 tgt agt ttt gaa gaa gca cga gaa gtt ttt gaa aac acg gaa aga aca        269
Cys Ser Phe Glu Glu Ala Arg Glu Val Phe Glu Asn Thr Glu Arg Thr
        25                  30                  35 act gaa ttt tgg aag cag tat gtt gat ggt gac cag tgt gag tcc aat        317
Thr Glu Phe Trp Lys Gln Tyr Val Asp Gly Asp Gln Cys Glu Ser Asn
    40                  45                  50 cca tgt tta aat ggc ggc agt tgc aag gat gac att aat tcc tat gaa        365
Pro Cys Leu Asn Gly Gly Ser Cys Lys Asp Asp Ile Asn Ser Tyr Glu
55                  60                  65                  70 tgt tgg tgt ccc ttt gga ttt gaa gga aag aac tgt gag ctc gat gta        413
Cys Trp Cys Pro Phe Gly Phe Glu Gly Lys Asn Cys Glu Leu Asp Val
                75                  80                  85 aca tgt aac att aag aat ggc aga tgc gag cag ttt tgt aaa aat agt        461
Thr Cys Asn Ile Lys Asn Gly Arg Cys Glu Gln Phe Cys Lys Asn Ser
            90                  95                 100 gct gat aac aag gtg gtt tgc tcc tgt act gag gga tat cga ctt gca        509
Ala Asp Asn Lys Val Val Cys Ser Cys Thr Glu Gly Tyr Arg Leu Ala
        105                 110                 115 gaa aac cag aag tcc tgt gaa cca gca gtg cca ttt cca tgc ggc cgc        557
Glu Asn Gln Lys Ser Cys Glu Pro Ala Val Pro Phe Pro Cys Gly Arg
    120                 125                 130 gtt tct gtt tca caa act tct aag ctc acc cgt gct gag act gtt ttt        605
Val Ser Val Ser Gln Thr Ser Lys Leu Thr Arg Ala Glu Thr Val Phe
135                 140                 145                 150 cct gat gtg gac tat gta aat tct act gaa gct gaa acc att ttg gat        653
Pro Asp Val Asp Tyr Val Asn Ser Thr Glu Ala Glu Thr Ile Leu Asp
                155                 160                 165 aac atc act caa agc acc caa tca ttt aat gac ttc act cgg gtt gtt        701
Asn Ile Thr Gln Ser Thr Gln Ser Phe Asn Asp Phe Thr Arg Val Val
            170                 175                 180 ggt gga gaa gat gcc aaa cca ggt caa ttc cct tgg cag gtt gtt ttg        749
Gly Gly Glu Asp Ala Lys Pro Gly Gln Phe Pro Trp Gln Val Val Leu
        185                 190                 195 aat ggt aaa gtt gat gca ttc tgt gga ggc tct atc gtt aat gaa aaa        797
Asn Gly Lys Val Asp Ala Phe Cys Gly Gly Ser Ile Val Asn Glu Lys
    200                 205                 210 tgg att gta act gct gcc cac tgt gtt gaa act ggt gtt aaa att aca        845
```

```
Trp Ile Val Thr Ala Ala His Cys Val Glu Thr Gly Val Lys Ile Thr
215                 220                 225                 230 gtt gtc gca ggt gaa cat aat att gag gag aca gaa cat aca gag caa        893
Val Val Ala Gly Glu His Asn Ile Glu Glu Thr Glu His Thr Glu Gln
                    235                 240                 245 aag cga aat gtg att cga att att cct cac cac aac tac aat gca gct        941
Lys Arg Asn Val Ile Arg Ile Ile Pro His His Asn Tyr Asn Ala Ala
                250                 255                 260 att aat aag tac aac cat gac att gcc ctt ctg gaa ctg gac gaa ccc        989
Ile Asn Lys Tyr Asn His Asp Ile Ala Leu Leu Glu Leu Asp Glu Pro
            265                 270                 275 tta gtg cta aac agc tac gtt aca cct att tgc att gct gac aag gaa       1037
Leu Val Leu Asn Ser Tyr Val Thr Pro Ile Cys Ile Ala Asp Lys Glu
        280                 285                 290 tac acg aac atc ttc ctc aaa ttt gga tct ggc tat gta agt ggc tgg       1085
Tyr Thr Asn Ile Phe Leu Lys Phe Gly Ser Gly Tyr Val Ser Gly Trp
295                 300                 305                 310 gga aga gtc ttc cac aaa ggg aga tca gct tta gtt ctt cag tac ctt       1133
Gly Arg Val Phe His Lys Gly Arg Ser Ala Leu Val Leu Gln Tyr Leu
                315                 320                 325 aga gtt cca ctt gtt gac cga gcc aca tgt ctt gct agc aca aag ttc       1181
Arg Val Pro Leu Val Asp Arg Ala Thr Cys Leu Ala Ser Thr Lys Phe
            330                 335                 340 acc atc tat aac aac atg ttc tgt gct ggc ttc cat gaa gga ggt aga       1229
Thr Ile Tyr Asn Asn Met Phe Cys Ala Gly Phe His Glu Gly Gly Arg
        345                 350                 355 gat tca tgt caa gga gat agt ggg gga ccc cat gtt act gaa gtg gaa       1277
Asp Ser Cys Gln Gly Asp Ser Gly Gly Pro His Val Thr Glu Val Glu
360                 365                 370 ggg acc agt ttc tta act gga att att agc tgg ggt gaa gag tgt gca       1325
Gly Thr Ser Phe Leu Thr Gly Ile Ile Ser Trp Gly Glu Glu Cys Ala
375                 380                 385                 390 atg aaa ggc aaa tat gga ata tat acc aag gta tcc cgg tat gtc aac       1373
Met Lys Gly Lys Tyr Gly Ile Tyr Thr Lys Val Ser Arg Tyr Val Asn
                395                 400                 405 tgg att aag gaa aaa aca aag ctc act taatgaaaga tggatttcca             1420
Trp Ile Lys Glu Lys Thr Lys Leu Thr
                410                 415 aggttaattc attggaattg aaaattaaca gggcctctca ctaactaatc actttcccat     1480
cttttgttag atttgaatat atacattcta tgatcattgc ttttttctctt tacaggggag    1540 aatttcatat tttacctgag caaattgatt agaaaatgga accactagag gaatataatg     1600
tgttaggaaa ttacagtcat ttctaagggc ccagcccttg acaaaattgt gaagttaaat     1660
tctccactct gtccatcaga tactatggtt ctccactatg caactaact cactcaattt      1720 tccctcctta gcagcattcc atcttcccga tcttctttgc ttcttcaacc aaaacatcaa     1780
tgtttattag ttctgtatac agtacaggat ctttggtcta ctctatcaca aggccagtac    1840
cacactcatg aagaaagaac acaggagtag ctgagaggct aaaactcatc aaaaacacta    1900
ctccttttcc tctaccctat tcctcaatct tttacctttt ccaaatccca atccccaaat    1960 cagttttct ctttcttact ccctctctcc cttttaccct ccatggtcgt taaggagag      2020 atggggagca tcattctgtt atacttctgt acacagttat acatgtctat caaacccaga   2080
cttgcttcca tagtggagac ttgcttttca gaacataggg atgaagtaag gtgcctgaaa   2140
agtttggggg aaaagtttct ttcagagagt taagttattt tatatatata atatatatat   2200
aaaatatata atatacaata taaatatata gtgtgtgtgt gtatgcgtgt gtgtagacac   2260
```

```
acacgcatac acacatataa tggaagcaat aagccattct aagagcttgt atggttatgg    2320
aggtctgact aggcatgatt tcacgaaggc aagattggca tatcattgta actaaaaaag    2380
ctgacattga cccagacata ttgtactctt tctaaaaata ataataataa tgctaacaga    2440
aagaagagaa ccgttcgttt gcaatctaca gctagtagag actttgagga agaattcaac    2500
agtgtgtctt caacagtgtt cagagccaag caagaagttg aagttgccta gaccagagga    2560
cataagtatc atgtctcctt taactagcat accccgaagt ggagaagggt gcagcaggct    2620
caaaggcata agtcattcca atcagccaac taagttgtcc ttttctggtt tcgtgttcac    2680
catggaacat tttgattata gttaatcctt ctatcttgaa tcttctagag agttgctgac    2740
caactgacgt atgtttccct ttgtgaatta ataaactggt gttctggttc at            2792
```

<210> SEQ ID NO 2
<211> LENGTH: 415
<212> TYPE: PRT
<213> ORGANISM: Homo sapiens

<400> SEQUENCE: 2

```
Tyr Asn Ser Gly Lys Leu Glu Glu Phe Val Gln Gly Asn Leu Glu Arg
 1               5                  10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285
```

```
Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305             310                 315                     320

Leu Val Leu Gln Tyr Leu Arg Val Pro Leu Val Asp Arg Ala Thr Cys
                325                 330                 335

Leu Ala Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415
```

US 6,531,298 B2

FACTOR IX ANTIHEMOPHILIC FACTOR WITH INCREASED CLOTTING ACTIVITY

RELATED APPLICATIONS

This application claims priority from provisional application Ser. No. 60/053,571, filed Jul. 21, 1997, the disclosure of which is incorporated by reference herein in its entirety.

This invention was made with Government support under Grant Number RO1-HL 38973 from the National Institutes of Health. The Government has certain rights to this invention.

FIELD OF THE INVENTION

This invention concerns Factor IX in general, and particularly concerns Factor IX containing a mutation that enhances the clotting activity thereof. This invention also concerns DNA constructs encoding such Factor IX, along with vectors containing such constructs.

BACKGROUND OF THE INVENTION

Factor IX (FIX; also known as "Christmas Factor") plays a key role in both the intrinsic and extrinsic coagulation pathways (E. Davie et al., *Biochemistry* 30, 10363 (1991); B. Furie and B. Furie, *Cell* 53, 505 (1988)). Human Factor IX and DNA encoding the same is disclosed in U.S. Pat. No. 4,994,371 to Davie et al., and in European Patent 0107278 to Brownlee.

FIX circulates as a 415 amino acid, single chain plasma zymogen (A. Vysotchin et al., *J. Biol. Chem.* 268, 8436 (1993)). The zymogen of FIX is activated by FXIa or by the tissue factor/FVIIa complex. Specific cleavages between arginine-alanine 145–146 and arginine-valine 180–181 result in a light chain and a heavy chain linked by a single disulfide bond between cysteine 132 and cysteine 289 (S. Bajaj et al., *Biochemistry* 22, 4047 (1983)). The structural organization of FIX is similar to that of the vitamin K-dependent blood clotting proteins FVII, FX and protein C (B. Furie and B. Furie, supra). The approximately 45 amino acids of the amino terminus comprise the gamma-carboxyglutamic acid, or gla, domain. This is followed by two epidermal growth factor homology domains (EGF), an activation peptide and the catalytic "heavy chain" which is a member of the serine protease family (A. Vysotchin et al., *J. Biol. Chem.* 268, 8436 (1993); S. Spitzer et al., *Biochemical Journal* 265, 219 (1990); H. Brandstetter et al., *Proc. Natl. Acad Sci. USA* 92, 9796 (1995)).

The major physiological function of FIXa in the blood coagulation cascade is to convert FX to FXa in a process that requires a phospholipid surface, calcium ions and FIXa's protein cofactor, FVIIIa. FIXa alone is an extremely poor protease but when bound to FVIIIa to form the "tenase" complex it becomes a potent FX activator(E. Duffy et al., *J. Biol. Chem.* 267, 17006 (1992); G. van Dieijen et al., *J. Biol. Chem.* 256, 3433 (1981)). It has been proposed that, upon binding FVIIIa, FIXa may undergo a conformational change at or near the active site (V. Mutucumarana et al., *J. Biol. Chem.* 267, 17012 (1992)). The importance of FIX is exemplified by the fact that patients with defective FIX molecules suffer from hemophilia B, an X-linked, recessive bleeding disorder which is clinically indistinguishable from hemophilia A in patients who have no FVIII function.

SUMMARY OF THE INVENTION

A first aspect of the present invention is a Factor IX protein having an amino acid substitution at amino acid position 338. Factor IX of the present invention is non-naturally occuring (e.g., does not contain only an arginine to proline substitution at amino acid position 338). The FIX proteins of the present invention advantageously have increased clotting activity as compared to the corresponding wild-type molecule.

A second aspect of the present invention is a pharmaceutical formulation comprising a mammalian Factor IX as described above in combination with a pharmaceutically acceptable carrier.

A third aspect of the present invention is a method of facilitating blood clotting in a subject in need of such treatment, comprising administering to the subject a mammalian Factor IX protein as described above, in an amount sufficient to facilitate or enhance blood clotting in said patient.

A forth aspect of the present invention is an isolated nucleic acid (e.g., a DNA or an RNA) encoding a mammalian Factor IX protein as described above.

A fifth aspect of the present invention is an expression cassette containing a nucleic acid encoding a mammalian Factor IX protein as described above.

A sixth aspect of the present invention is a gene transfer vector containing an expression cassette as described above.

An illustrative nucleic acid of the present invention is provided herein as SEQ ID NO:1, and an illustrative Factor IX amino acid sequence of the present invention is provided herein as SEQ ID NO:2.

The foregoing and other objects and aspects of the present invention are explained in greater detail in the drawings herein and the specification set forth below.

BRIEF DESCRIPTION OF THE DRAWINGS

FIGS. 2A–2C. Kinetics of FX activation by R338A-FIXa and wt-FIXa.

FIG. 2A: In the absence of FVIIIa. Twenty five nM of R338A-FIXa (open squares) or wt-FIXa (closed squares) in 5 mM $CaCl_2$ and 100 µM PSPC vesicles were incubated with FX concentrations from 0 to 200 nM. Data represent the mean±SD of four values for each concentration of FX. The Km and Vmax values for R338A-FIXa were 53.50±7.44 nM, 2.58±0.13 nM FX/min respectively. For wt-FIXa, the Km was 28.45±3.56 nM, and Vmax was 2.55±0.09 nM FXa/min.

FIG. 2B: In the presence of 0.01 nM FVIIIa. 0.25 nM of R338A-FIXa (open squares) or wt-FIXa (closed squares) was used to activated FX in the presence 0.1 nM FVIIIa. Each concentration of FX is represented by the mean±SD of 6 values. The Km for R338A-FIXa was 7.72±0.65 nM, and Vmax was 2.47±0.04 nM FXa/min; for wt-FIXa, the Km was 18.38±3.37 nM, and Vmax was 0.64±0.03 nM FXa/min.

FIG. 2C: In the presence of 0.4 nM FVIIIa. FVIIIa (0.4 nM) was incubated with 0.25 nM of R338A-FIXa (open squares) or wtFIXa (closed squares), then used to activate FX. Each concentration of FX is the mean±SD of 6 values. The Km and Vmax were 12.23±0.84 nM, 5.42±0.08 nM FXa/min for R338A-FIXa; 19.64±1.79 nM, 2.46±0.06 nM FXa/min for wtFIXa. All of the curves were determined from fitting the data to Michaelis Menten equation.

DETAILED DESCRIPTION OF THE INVENTION

Figure 1:
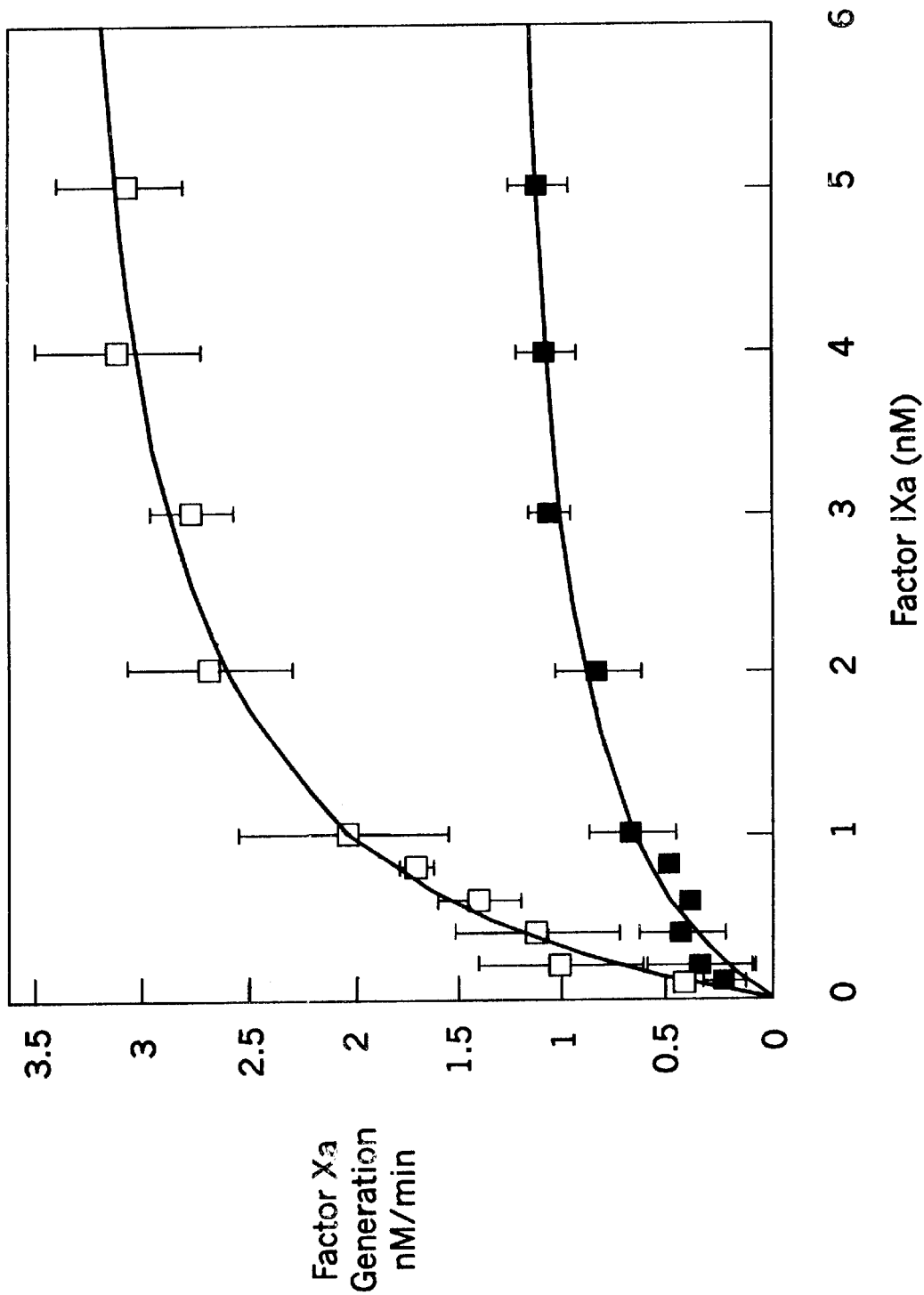
FIG. 1. Binding of mutant R338A-FIXa and wt-FIXa to their cofactor, FVIIIa. The effect of binding R338A-FIXa (open squares) and wt-FIXa (close squares) to FIX's cofactor, FVIIIa, was assessed in the presence of 100 M PSPC vesicles at 5 mM $CaCl_2$. FVIII (0.1 nM) was activated by thrombin and after 5 min the thrombin was inhibited by 100 nM hirudin. Binding was measured by FIXa-FVIIIa mediated FXa generation as described in the *Experimental procedures* section. Data represent the mean±SD of ten time points. The Kd and Bmax values of the R338A-FIX were 0.75±0.10 nM, and 3.56±0.15 nM FXa/min, respectively. For wt-FIXa, the Kd was 1.01±0.24 nM and Bmax was 1.30±0.10 nM FXa/min.

As noted above, the present invention provides a mammalian Factor IX protein having an amino acid substitution at amino acid position 338. The Arginine at amino acid position 338 is known in the art (see, e.g., F. Giannelli et al., *Nucleic Acids Res.* 18, 4053 (1990)(Arg 338 replaced with stop codon produces hemophilia B); R. Ketterling et al., *Am. J. Hum. Genet.* 54, 831 (1994)(Arg to Pro mutation at amino acid position 338 results in mild hemophilia B)). Substitutions of the inventions are, for example, a substitution of an arginine residue for an amino acid residue selected from the group consisting of alanine, valine, leucine, isoleucine, phenylalanine, tryptophan, methionine, glycine, serine, and threonine. In preferred embodiments of the invention, the substitution is a substitution of an arginine residue for an amino acid residue selected from the group consisting of alanine, leucine, and valine.

Factor IX of the present invention may be of any suitable origin. Factor IX will, in general, be mammalian factor IX (e.g., dog, cat, horse, cow, or pig Factor IX), but in a preferred embodiment is human Factor IX. Factor IX of the present invention converts Factor X to Factor Xa in the mammalian blood coagulation cascade, in a process that requires a phospholipid surface, calcium ions and the cofactor Factor VIIIa.

Factor IX of the present invention may be produced by recombinant means, as discussed in greater detail below, with the amino acid substitution at position 338 created by introducing a missense mutation into the DNA encoding the Factor IX by any suitable means, such as site-directed mutagenesis (see, e.g., U.S. Pat. No. 4,873,192 to Kunkel). Other mutations at other locations may be introduced as desired, as is known in the art. See, e.g., U.S. Pat. No. 4,994,371 to Davie et al.; U.S. Pat. No. 5,521,070 to Meulien. Position 338 herein preferably refers to position 338 of human FIX, or the homologous or corresponding position in other mammalian FIX proteins. FIX molecules of the present invention preferably have two to three times more coagulant activity than the corresponding wild type or plasma FIX. The increased activity may be the result of a two to three fold increase in kcat and/or a decrease (e.g., a twofold decrease) in Km.

Pharmaceutical formulations of the present invention comprise a Factor IX as described herein in combination with a pharmaceutically acceptable carrier, such as an aqueous carrier. Thus, formulations for use in carrying out the present invention include, but are not limited to, those suitable for intraveneous and intraarterial administration. The formulations may be conveniently presented in unit dosage form and may be prepared by any of the methods well known in the art.

Method of facilitating blood clotting in a subject in need of such treatment, such as a subject afflicted with hemophilia B, comprise administering to the subject a Factor IX protein as described above, in an amount sufficient to facilitate or enhance blood clotting in said subject. While the present invention is primarily contemplated to be for the treatment of human subjects, animal subjects such as dogs, cats, horses, etc. may also be treated by the compounds and methods of the present invention for veterinary purposes.

The production of cloned genes, isolated DNA, recombinant DNA, vectors, transformed host cells, proteins and protein fragments of the present invention may be carried out by well known genetic engineering techniques (see, e.g., U.S. Pat. No. 4,761,371 to Bell et al; U.S. Pat. No. 4,877,729 to Clark et al; U.S. Pat. No. 4,912,038 to Schilling et al; U.S. Pat. No. 4,879,224 to Wallher).

A vector is a replicable DNA or RNA construct. Vectors are used to either amplify nucleic acids encoding the protein of the present invention or to express the proteins of the present invention. An expression vector is a replicable nucleic acid construct in which a nucleic acid sequence encoding the protein of the invention is operably linked to suitable control sequences capable of effecting the expression of proteins of the invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences that control the termination of transcription and translation. The control sequences are operably associated with a nucleic acid to be expressed on a common nucleic acid to provide a recombinant expression cassette (on a nucleic acid molecule) which is carried by the vector into the target cell of interest. As will be apparent to those skilled in the art, the expression cassette is a DNA when the vector is a DNA virus; and the expression cassette is an RNA when the vector is an RNA virus. Amplification vectors do not require expression control domains: all that is needed is the ability to replicate in a host, usually conferred by an origin of replication, and a selection gene to facilitate recognition of transformants. Vectors typically comprise plasmids, viruses (e.g., papillomavirus, adenovirus, adeno-associated virus, cytomegalovirus), phage, retroviruses and integratable DNA fragments. The vectors may be used to produce recombinant Factor IX, or may be used in gene therapy to administer the expression cassette to targetted cells within the patient and produce the Factor IX in the patient.

Methods of making a recombinant Factor IX as described herein typically comprise maintaining a culture of cells transformed with a gene transfer vector as described above (or carrying an expression cassette as described above) under conditions that permit, or are suitable for, the expression of Factor IX, and then collecting the Factor IX from the cell culture. Preferably the cells in the culture are cells that co-express a vitamin K-dependent carboxylase, and the production of the Factor IX is carried out so that the Factor IX is carboxylated, as described in U.S. Pat. No. 5,268,275 to Stafford and Wu (the disclosure of which is incorporated herein by reference). The recombinant Factor IX can be produced in transgenic cow or sheep milk in accordance with known techniques.

In the Examples below, the abbreviations used are: FIX, factor IX; FIXa, activated factor IX; wt-FIX refers to wild type factor IX; R338A-FIX refers to a FIX of the present invention in which the amino acid at position 338 is an alanine; FVII, factor VII; FX, factor X; FXIa, activated factor XI; FVIIIa, activated factor VIII; FIX-Xegf1, factor IX with the egf1 domain substituted by that of factor X; gla, the gamma-carboxyglutamic acid-rich domain; PSPC, phosphotidylserine and phosphotidylcholine; aPTT, one stage activated partial thromboplastin time assay; PTT, partial thromboplastin time, SDS-PAGE, SDS-polyacrylamide gel electrophoresis.

EXAMPLES

Using recombinant techniques we created mutant FIX molecules designed to locate the residues of FIXa that bind FVIIIa. We have found one mutation, R338A-FIX, whose clotting activity is two and one half to three times that of wild type FIX. In an attempt to understand the causes contributing to the increased clotting activity of R338A-FIX, we have determined several functional parameters. Our results demonstrate that the increased clotting activity is FVIIIa-dependent and is due to an increased kcat and decreased Km for FX, the substrate for the FIXa/FVIIIa complex.

I. Experimental procedures

A. Materials

Oligonucleotides for in vitro mutagenesis were purchased from Gibco BRL Life Technologies (Grand Island, N.Y.). T7 DNA polymerase, T4 DNA ligase and restriction enzymes were obtained from New England Biolabs (Beverly, Mass.). Sequenase 7-deaza-dGTP DNA sequencing kits were purchased from USB (Cleveland, Ohio). The anti-human FIX monoclonal antibodies used in this study were A-1, A-5, and A-7, a gift from Dr. Kenneth J. Smith. Purified normal human plasma FIX, FX, FXa, FXIa and thrombin were purchased from Enzyme Research Laboratories Inc. (South Bend, Ind.). Coagulation control level 1, FIX deficient plasma, FVIII deficient plasma, and aPTT reagent were obtained from Sigma Chemical Company (St. Louis, Mo.). Purified normal human plasma FVIII was a gift from Rohrer Biotechnology Inc. (Springfield, Va.). Phosphatidylserine and phosphatidylcholine were purchased from Avanti Polar Lipids (Alabaster, Ala.). Spectrozyme FXa was obtained from American Diagonostica Inc. (Greenwich, Conn.). Hirudin was obtained from Accurate Chemical and Scientific Corp. (Westbury, N.Y.). All other reagents were of the highest purity available.

B. Methods

In vitro mutagenesis and construction of the expression plasmid: Site-directed mutagenesis was performed as described by Kunkel, *Proc. Nat'l Acad. Sci. USA* 82, 488 (1985). The entire cDNA sequence was determined to ensure that the mutation was correct and that no inadvertent mutations had been introduced.

Expression and purification of recombinant proteins: Human embryo kidney 293 cells were grown in a mixture of Dulbecco's modified Eagle medium and F-12 medium (DMEM/F12), supplemented with 10% fetal calf serum. FIX and its mutants, in the vector pCMV5 (S. Andersson et al., *J. Biol. Chem.* 264, 8222 (1989)), were cotransfected with a pSV2 neo selection marker, using the calcium phosphate coprecipitation method (N. Hamaguchi et al., *J. Biol. Chem.* 266, 15213 (1991)). G418-resistant cell clones were subcloned and expanded. The supernatants from each clone were collected and assayed for FIX expression using an immunoradiometric assay with FIX antibodies. Stable clones with high expression levels of FIX were expanded and transferred into 850 $cm^2$ roller bottles for protein production. For production of FIX, serum free DMEM/F12 was supplemented with 100 units/ml penicillin, 100 $\mu$g/ml streptomycin, 5 $\mu$g/ml vitamin K and 10 mg of insulin-transferrin-sodium selenite per liter. The supernatants were collected every 24 hours for 10–15 days and stored at $-20°$ C. For purification, the frozen supernatants were thawed and EDTA and benzamidine-HCl were added (final concentration 4 mM and 5 mM respectively). The supernatants were filtered through a 0.45 $\mu$M millipore filter to remove cell debris and incubated at 4° C. with overnight shaking in Q sepharose fast flow resin (2.5 ml resin per liter of supernatant). The resin was pre-equilibrated in 20 mM Tris-HCl, 15 mM NaCl, 2mM benzamidine-HCl pH7.4 (equilibration buffer). The resin was loaded in a column, washed with equilibration buffer containing 2 mM EDTA for 4 hours, and washed for another 1 hour with equilibration buffer. FIX was eluted from the column with a 0–60 mM calcium gradient, concentrated in a centriprep-30, and stored at $-80°$ C.

Iodination of proteins: 100 kg of monoclonal antibodies were labeled with $^{125}$I-Na using iodobeads according to the manufacturer's instructions (Pierce, Rockford, Ill.). The radiolabeled antibodies were separated from free $^{125}$I on sephadex G-25. The specific activities of labeled antibodies averaged about $3.6 \times 10^6$ cpm/$\mu$g of protein.

Radioimmunometric assay: Three monoclonal antibodies (A1, A5, and A7) were used. A5 was employed at 10 $\mu$g/ml in 50 mM $NaHCO_3$ (pH8.5) to coat a 96 well microtiter plate. Samples were added to the antibody-coated wells. After incubation at 4° C. overnight, the second $^{125}$I antibody, A1 or A7, was added to about $1 \times 10^5$ cpm/well. After a 4 hour incubation, unbound radioactive antibody was removed by washing with 20 mM Tris-HCl, 150 mM NaCl, 5 mM $CaCl_2$, and 1 mM $MgCl_2$, pH7.5 and the samples were counted. Standard curves were constructed using plasma FIX as a standard.

Analysis of Recombinant FIX: SDS-PAGE was performed as described by U. Laemmli, *Nature* 227, 680 (1970). Following electrophoresis, the purified proteins were visualized by silver staining or western blotting employing $^{125}$I labeled FIX monoclonal antibodies. The concentration of purified FIX was determined assuming an extinction coefficient $\epsilon^{1\%}$ of 13.3. Analyses of Gla content were kindly performed by Dr. Cindy Payne at Lilly Research Laboratories.

Clotting Assay: One-stage activated partial thromboplastin time (aPTT) assays were performed according to the manufacturer's instructions (Sigma). For partial thromboplastin time (PTT) assays, the FIX proteins were activated prior to the clotting assay and phospholipids were used instead of activator. The ability of the sample to correct the clotting time of FIX-deficient plasma was compared to a standard curve utilizing purified plasma FIX. All assays were repeated at least three times.

Activation of FIX by FXIa: wt-FIX or R338A-FIX was incubated with FXIa at a molar ratio 100:1 in 20 mM HEPES, 150 mM NaCl, 5 mM $CaCl_2$, pH 7.4 at 37° C. for 2 hours. The process of activation was followed by removing aliquots at specific time points. The reaction was stopped by adding SDS and 2-mercaptoethanol; the samples were immediately boiled for 5 min and run on SDS-PAGE. Completely activated samples, judged by SDS-PAGE, were aliquoted and stored at −80° C.

Activation of VIII by thrombin: FVIII (10 nM) was activated to FVIIIa in HEPES buffer containing 20 nM thrombin for 5 min at 25° C. The thrombin was then inhibited by further incubation with 100 nM hirudin, calcium and PSPC vesicles for an additional 5 min at 25° C. The concentration of FVIII was estimated from its activity in a one-stage aPTT assay assuming the concentration of FVIII in plasma to be 0.3 nM.

Kd determinations for the FIXa-FVIIIa interaction: Freshly prepared 0.1 nM FVIIIa was incubated with concentrations of FIXa varying from 0 to 5 nM for 5 min at 25° C. in HEPES buffer plus 5 mM calcium, 100 $\mu$M PSPC. FX (100 nM) and 0.5 mM spectrozyme-FXa were then added and the initial rate of FXa generation was determined.

FX activation by FIXa in the presence of phospholipid: 50 nM of wt-FIXa or mutant R338A-FIXa was incubated with 200 M PSPC vesicles, 10 mM calcium and 0.5 mM spectrozyme FXa in a microplate well for 5 min at 25° C. Varying concentrations of FX (between 0–400 nM) were added to this mixture and the absorbance at 405 nm was measured on a Vmax microplate reader. The final concentration were 25 nM FIXa, 100 $\mu$M PSPC, 0–200 nM FX and 0.25 mM spectrozyme FXa.

FX activation by FIXa in the presence of phospholipid and FVIIIa: The assay was performed by incubating freshly prepared FVIIIa with a fixed concentration of FIXa (0.5 nM) for 5 min at 25° C. in HEPES buffer plus 200 $\mu$M PSPC, 10 mM calcium, and 0.5 mM spectrozyme FXa for a final volume of 50 $\mu$l. FVIIIa was prepared as described above. Reactions were initiated by the addition of 50 $\mu$l of varying concentrations of FX (total volume 100 $\mu$l). The rate of generation of FXa was determined on a Vmax microplate reader. Final concentrations were 0.25 nM FIXa, 0.1 nM or 0.4 nM FVIIIa, 100 $\mu$M PSPC, 0–200 nM FX and 0.25 mM spectrozyme FXa.

The effect of hirudin on the binding assay: The experiments were performed as described for FIXa binding to FVIIIa, except that in one group 100 nM hirudin was added to inhibit thrombin activity and in the other group no hirudin was added.

Potential proteolysis of FIXa by FXa and FVIIIa: Purified plasma wt-FIXa (2000 nM), FXa (300 nM), FVIIIa (0.15 nM), and Ca$^{2+}$ (5 mM) were mixed and incubated at 25° C. At different times, samples were removed, subjected to SDS-PAGE and then silver stained.

C. Data Analysis

FIXa activity: This is determined from several standard assays. The data for the initial rate of FIXa-mediated FX activation can be converted to nM Xa/min by using the following equation (M. Griffith et al., *Journal of Clinical Investigation* 75, 4 (1985); P. Larson et al., *J. Biol. Chem.* 271, 3869 (1996)):

$$\text{absorbance} = at^2 + bt + c \quad \text{equation (1)}$$

where a gives the rate at which FXa cleaves the chromogenic substrate or the rate at which FX is cleaved; b gives the amount of FXa present in the zymogen FX; c gives the amount of cleaved substrate at time 0.

The kd for FIXa binding to FVIIIa was determined using the quadratic equation described by Krishnaswamy (*J. Biol. Chem.* 267, 23696 (1992)) (equation 2) where it is assumed that the rate of FXa cleavage is directly proportional to the FIXa-FVIIIa complex. The data were fit with Kaleidoscope or Mathematica.

II. Results

The expression and purification of mutant R338A-FIX or recombinant wt-FIX: The expression level of the carboxylated FIX varied from 500–1000 ng/10$^6$ cell/24 hr. SDS-PAGE analysis demonstrated that both purified R338A-FIX and recombinant wt-FIX migrated as a single band with the same molecular weight as plasma FIX (data not shown) and Gla analysis showed full carboxylation of both mutant R338A-FIX and recombinant wt-FIX (Table 1), further indicating the high purity of the expressed proteins. In addition both R338A-FIX and recombinant wt-FIX bound to three FIX-specific monoclonal antibodies with the same efficiency as to plasma-purified FIX or pooled normal plasma (Table 1).

TABLE 1

Antigenicity, γ-carboxyglutamic acid content and clotting activity of R338A-FIX and wt-FIX.

| Sample | Antigenicity | Gla | aPTT (%) | PTT (%) |
|---|---|---|---|---|
| R338A | 102% ± 9 | 13 | 260 ± 41 | 282 ± 53 |
| recombinant wt-FIX | 111% ± 2 | 11.1 | ND | 110 ± 16 |
| plasma purified FIX | 100 | 13.5 | 100 | 100 |
| pooled normal plasma | 100 | 12* | 94 ± 18 | ND |

Antigenicity is shown relative to pooled normal plasma FIX. The wells were coated with MoAb A5 and $^{125}$I-labeled A1 MoAb was used as a second antibody. Purified pooled plasma FIX was used to construct a standard curve for both the aPTT and PTT assays.
*The expected number of Gla residues per FIX molecule is 12.

Clotting activity: The initial characterization of recombinant FIX was a one-stage aPTT assay. Plasma purified FIX and normal pooled plasma were employed as standards. The results, shown in Table 1, indicate that R338A-FIX exhibited a 2.6 fold increase in clotting activity. To rule out the possibility that the increased clotting activity exhibited by R338A-FIX was due to trace amounts of FIXa generated during protein purification, all FIXs were activated and assayed in FIX-deficient plasma. As shown in table 1, the clotting activity of activated R338A-FIX was 2.8 fold higher than activated plasma FIX. This result agrees well with results of the aPTT assay and suggests that the increased activity is not the result of activated FIXa contaminating the R338A-FIX preparation.

FIXa binding to FVIIIa: To monitor FIXa-FVIIIa complex formation, it was assumed that activity is directly proportional to the concentration of the FIXa-FVIIIa complex (P. Larson et al., *J. Biol. Chem.* 271, 3869 (1996)). This is a reasonable assumption because, in the conditions that we use, addition of FVIIIa to FIXa results in a 300 to 1,000 fold increase in the reaction rate. The results of five experiments, each done in duplicate, are shown in FIG. 1 and in Table 2. When the data were fit to equation 2, the apparent dissociation constant (Kd) for binding of R338A-FIXa to FVIIIa was 0.75±0.10 nM for R338A-FIXa compared to 1.01±0.24 nM for plasma FIXa. The maximum rate of FX cleavage achieved, however, was 2.7 fold greater for activated R338A-FIX than for wt-FIXa (3.56±0.15 nM FXa/min and 1.30±0.10 nM/min, respectively).

TABLE 2

Kinetic analyses of mutant R338A-FIXa and wt-FIXa.

| | Km nM | Vmax nM FXa min$^{-1}$ | enzyme nM | Kcat* s$^{-1}$ | Kcat/Km** |
|---|---|---|---|---|---|
| without FVIIIa | | | | | |
| $_{wt}$FIXa | 28.45 ± 3.56 | 2.55 ± 0.09 | 25 | 1.6 × 10$^{-3}$ | 5.62 × 10$^4$ |
| R338A FIXa | 53.50 ± 7.44 | 2.58 ± 0.13 | 25 | 1.6 × 10$^{-3}$ | 2.99 × 10$^4$ |
| with FVIIIa 0.1 nM | | | | | |
| $_{wt}$FIXa | 18.38 ± 3.37 | 0.63 ± 0.03 | 0.02 | 0.50 | 2.72 × 10$^7$ |
| R338A FIXa | 7.72 ± 0.65 | 2.47 ± 0.04 | 0.03 | 1.33 | 1.72 × 10$^8$ |
| with FVIIIa 0.4 nM | | | | | |
| $_{wt}$FIXa | 19.64 ± 1.79 | 2.46 ± 0.06 | 0.08 | 0.50 | 2.50 × 10$^7$ |
| R338A FIXa | 12.23 ± 0.84 | 5.42 ± 0.08 | 0.08 | 1.13 | 9.24 × 10$^7$ |

*Kcat values were calculated by: Kcat = Vmax/(enzyme), in the presence of FVIIIa, the enzyme concentrations of the FIXa-FVIIIa complex were calculated based on equation 2 and the observed Kd values.
**Units are M FXa and M$^{-1}$ FIXa (or FIXa-FVIIIa), 1 s$^{-1}$.

Figure 2A:
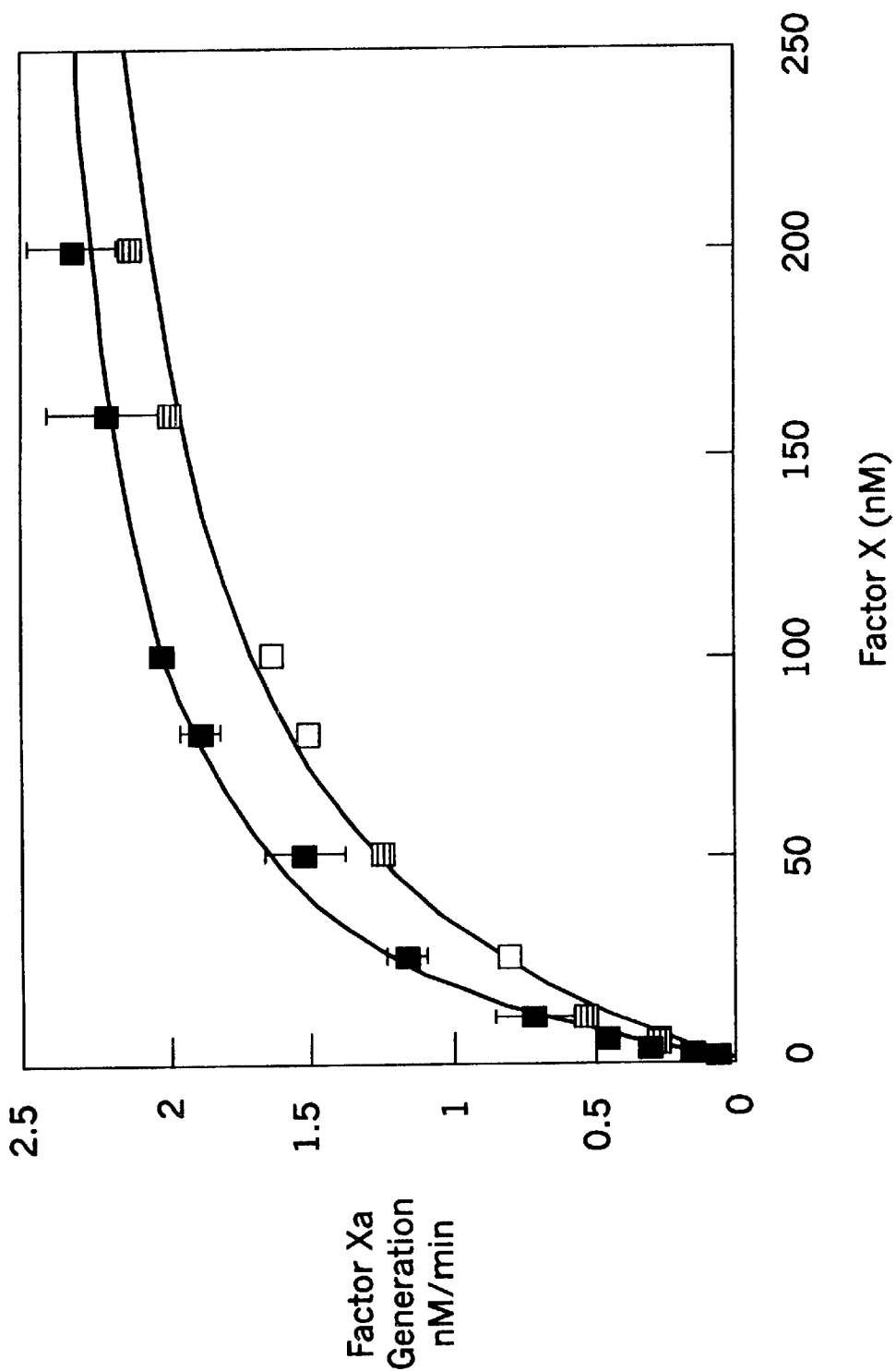

FX activation by FIXa in the absence or presence of cofactor FVIIIa: The kinetic parameters for cleavage of FX by R338A-FIXa, plasma FIXa, or recombinant wt-FIXa were investigated in the absence or presence of their cofactor, FVIIIa. In the absence of FVIIIa, the kcat for both R338A-FIXa and wt-FIXa was 1.6×10$^{-3}$/s. The Km value for R338A-FIXa was increased about 2 fold compared to recombinant FIXa (FIG. 2a). When FVIIIa at either 0.1 nM (FIG. 2b) or 0.4 nM (FIG. 2c) was included in the reaction, the kcat of R338A-FIXa was 1.33 and 1.13/sec respectively, compared to 0.5/sec for recombinant wt-FIX (Table 2). Moreover, in contrast to the situation in the absence of FVIIIa, where the Km value of R338A-FIXa was increased when compared to recombinant wt-FIX, the Km of R338A-FIXa was decreased about 2 fold compared to wt-FIXa (Table 2).

Figure 3:
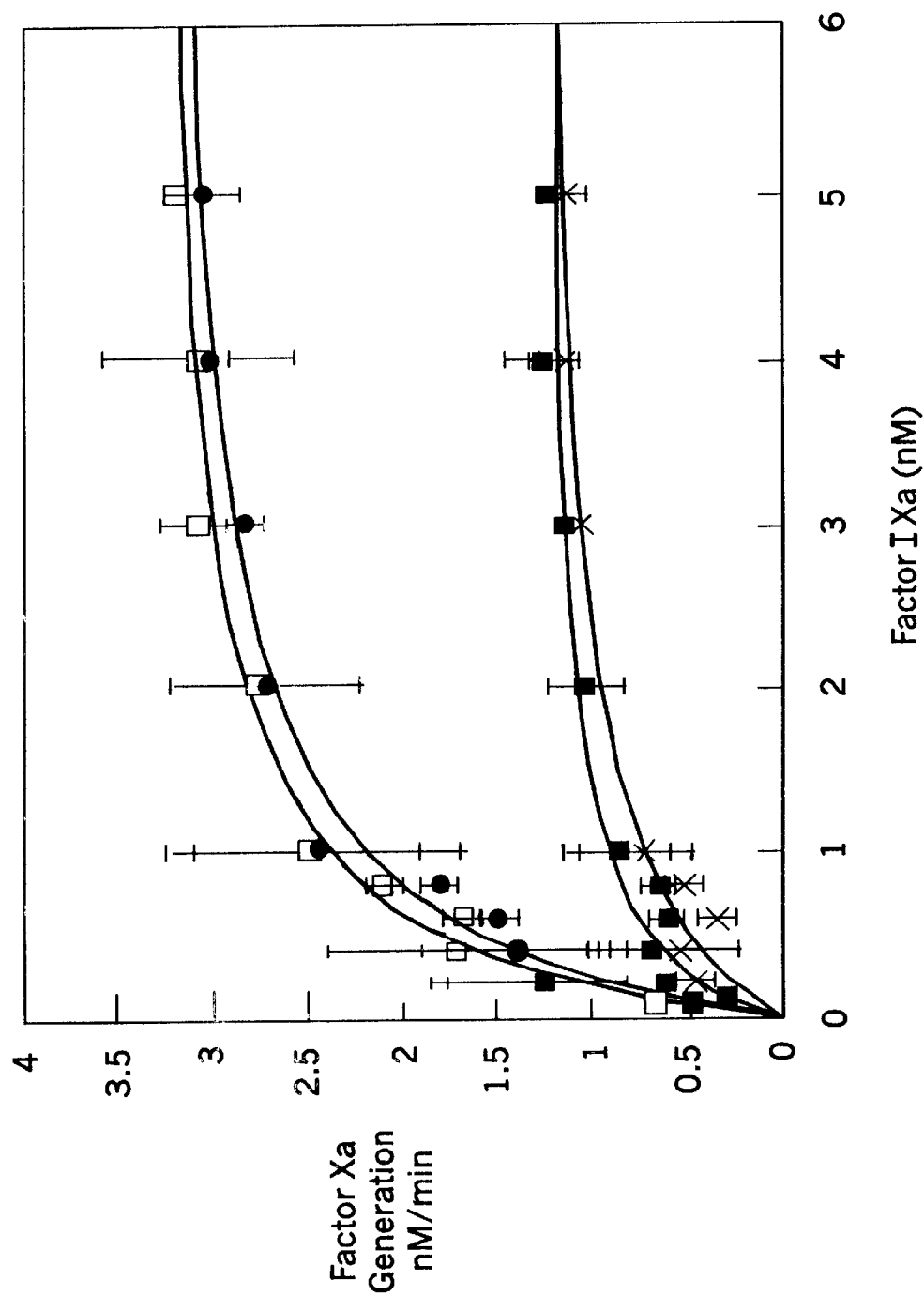
FIG. 3. The effect of hirudin on the R338A-FIXa or wt-FIXa binding to its cofactor FVIIIa. In parallel experiments, the effect of hirudin on the binding of R338AFIXa or wt-FIXa to FVIIIa was determined. The methods were as described in FIG. 1. In the presence (cross) or absence (filled squares) of 100 nM hirudin the Kd and Bmax of wt-FIXa were similar; 0.85±0.29 nM and 1.35±0.15 nM FXa/min in the presence of hirudin and 0.38±0.15 nM and 1.27±0.12 nM FXa/min in its absence. For R338-FIXa, the Kd and Bmax in the presence of 100 nM hirudin (filled circles) were 0.51±0.11 nM and 3.38±0.19 nM FXa/min while in the absence of hirudin (open squares) the values were 0.40±0.06 nM, 3.39±0.12 nM FXa/min. Each point is the mean of 4 determinations with the standard deviations shown.

The effect of hirudin on the mutant R338A-FIXa and wt-FIXa binding to its cofactor FVIIIa: One obvious possibility for the increased activity of R338A-FIX is that replacing the arginine by an alanine eliminates a potential proteolytic cleavage site. It has been reported, for example, that thrombin can cleave FIX after residue 338 (C170) to render the FIX molecule inactive (D. Enfield, Blood 64, 821 (1984); W. Kisiel et al., Blood 66, 1302 (1985)). This did not seem likely because the experiments which demonstrated this phenomenon required very large concentrations of thrombin. Because hirudin is a potent inhibitor of thrombin we repeated our binding experiments in the presence and absence of hirudin. As shown in FIG. 3, hirudin had no detectible effect on the maximum velocity achieved with recombinant wt-FIX. Vmax was 1.27±0.12 nM FXa/min in the absence of hirudin, and 1.35±0.15 nM FXa/min in its presence. Thus, the cleavage of FIXa at arginine 338 (C170) by thrombin does not explain the increased catalytic activity of R338A-FIX.

Potential cleavage of FIXa by FXa and FVIIIa: Another potential source of proteolysis in our experiment system is the FXa generated during the reaction. As far as we are aware, there is no report of an attempt to cleave FIX by FXa in the presence of FVIIIa. To test the possibility that FXa in the presence of FVIIIa might cleave the heavy chain of FIXa, we incubated purified plasma FIXa with FXa and FVIIIa. If FXa can cleave FIXa at arginine 338 (C170), it would be easily observed by SDS-PAGE. No cleavage in the heavy chain of FIXa (MW 28000) was observed when incubated for up to 120 minutes (data not shown). Thus, reduced proteolysis of R338A-FIX compared to wt-FIX does not explain the increase in catalytic activity.

Discussion. Our original aim was to identify residues critical for the interaction between FIXa and FVIIIa. Instead we found a mutation, arginine 338 (C170) to alanine, that resulted in a FIXa molecule with three times more coagulant activity than wild type or plasma FIX. The increased activity depends on the presence of FVIIIa and is the result of a 2.7-fold increase in kcat and a twofold decrease in Km. In the absence of FVIIIa, the Km for R338A-FIXa (53 nM) is about twofold higher than for wild type FIXa while in its presence it is twofold lower (7.7 nM). Thus, in the presence of FVIIIa, R338A-FIXa's Km for its substrate FX is decreased 7-fold while wt-FIX's Km decreased only 1.5 fold relative to their rates in the absence of FVIIIa.

In an attempt to rationalize this observation we turned to the x-ray structure of porcine FIXa (H. Brandstetter et al., Proc. Natl. Acad Sci. USA 92), 9796 (1995)). Arginine 338 (C170) is found in a surface alpha-helix which starts at leucine 330 (C162), terminates at arginine 338 (C170), and is anchored by a disulfide bond between cysteine 336 (C168) and cysteine 350 (C182). Arginine 338 (C170) also forms a hydrogen bond through its guanido group to the hydroxyl group of threonine 335 (C167); the hydroxyl group of threonine 335 (C167) in turn forms a hydrogen bond to one of the carboxylate oxygens of aspartate 332 (C164) (not shown). The helix that contains arginine 338 (C170) seems to be important for FIX's function because it contains numerous missense mutations which result in hemophilia B. The only known missense mutation at 338 (C170) is a proline for arginine which results in moderate hemophilia B with 16% of normal activity but only 27% normal antigen level. However, mutations of leucine 330 (C 162) to proline, valine 331 (C163) to alanine or aspartate, aspartate 332 (C164) to tyrosine, arginine 333 (C165) to glycine, glutamine or leucine, alanine 334 (C166) to threonine or aspartate and leucine 337 (C169) to isoleucine, proline or phenylalanine all cause severe hemophilia B even though their antigen levels are near normal.

The foregoing is illustrative of the present invention, and is not to be construed as limiting thereof. The invention is defined by the following claims, with equivalents of the claims to be included therein.

That which is claimed is:

1. An isolated nucleic acid encoding a human Factor IX protein having an amino acid at amino acid position 338;
   wherein said nucleic acid encodes an amino acid residue selected from the group consisting of alanine, valine, isoleucine, phenylalanine, tryptophan, methionine, serine, and threonine at position 338;
   wherein said amino acid position 338 corresponds to position 338 of SEQ ID NO: 2.

2. An isolated nucleic acid according to claim 1, wherein said nucleic acid is a DNA.

3. An isolated nucleic acid according to claim 1, wherein said nucleic acid encodes an amino acid residue selected from the group consisting of alanine and valine at position 338.

4. An expression cassette containing a nucleic acid encoding a human Factor IX protein, said human Factor IX protein having an amino acid at amino acid position 338;
   wherein said nucleic acid encodes an amino acid residue selected from the group consisting of alanine, valine, leucine, isoleucine, phenylalanine, tryptophan, methionine, serine, and threonine at position 338;
   wherein said amino acid position 338 corresponds to position 338 of SEQ ID NO: 2.

5. A gene transfer vector containing an expression cassette according to claim 4.

6. A gene transfer vector according to claim 5, wherein said expression cassette is a DNA and said vector is a DNA virus.

7. A gene transfer vector according to claim 5, wherein said expression cassette is an RNA and said vector is an RNA virus.

8. A cell culture comprising cells transformed with a gene transfer vector according to claim 5.

9. A method of making a recombinant Factor IX, comprising maintaining a cell culture according to claim 5 under conditions that permit the expression of Factor IX, and then collecting said Factor IX from said cell culture.

10. A method according to claim 9, wherein the cells of said culture co-express a vitamin K-dependent carboxylase.

11. An isolated nucleic acid according to claim 1 encoding the protein having the sequence given herein as SEQ ID NO: 2.

12. An isolated nucleic acid according to claim 1 having the sequence given herein as SEQ ID NO: 1.

* * * * *

UNITED STATES PATENT AND TRADEMARK OFFICE
CERTIFICATE OF CORRECTION

PATENT NO. : 6,531,298 B2
DATED : March 11, 2003
INVENTOR(S) : Stafford et al.

It is certified that error appears in the above-identified patent and that said Letters Patent is hereby corrected as shown below:

<u>Title page,</u>
Item [57], ABSTRACT,
Line 12, should read as follows:
-- the same and vectors containing such nucleic acids. --

<u>Column 18,</u>
Line 37, should read as follows:
-- prising maintaining a cell culture according to claim 8 under --

Signed and Sealed this

Twelfth Day of August, 2003

JAMES E. ROGAN
*Director of the United States Patent and Trademark Office*